(12) United States Patent
Boehm

(10) Patent No.: US 6,485,516 B2
(45) Date of Patent: Nov. 26, 2002

(54) ACCOMMODATING IO-LENS EYES

(76) Inventor: Hans-Georg Boehm, Kellergrundweg 13, D-61476 Kronberg/Ts (DE)

(*) Notice: Subject to any disclaimer, the term of this patent is extended or adjusted under 35 U.S.C. 154(b) by 0 days.

(21) Appl. No.: 09/735,827

(22) Filed: Dec. 13, 2000

(65) Prior Publication Data
US 2002/0095212 A1 Jul. 18, 2002

(30) Foreign Application Priority Data
Dec. 14, 1999 (DE) .......................................... 199 60 136

(51) Int. Cl.[7] .................................................. A61F 2/16
(52) U.S. Cl. ...................... 623/6.49; 623/6.43; 623/6.38
(58) Field of Search ............................... 623/6.21, 6.37, 623/6.38, 6.39, 6.43, 6.47, 6.49

(56) References Cited

U.S. PATENT DOCUMENTS

| 4,254,509 A | 3/1981 | Tennant | 3/13 |
| 4,409,691 A | 10/1983 | Levy | 3/13 |
| 4,790,847 A | 12/1988 | Woods | 623/6 |
| 5,476,514 A | 12/1995 | Cumming | 623/6 |
| 5,609,630 A | * 3/1997 | Crozafon | 623/6 |

* cited by examiner

Primary Examiner—Dinh X. Nguyen
(74) Attorney, Agent, or Firm—Vidas, Arrett & Steinkraus, P.A.

(57) ABSTRACT

Artificial eye lenses which are to be replaced against the muddy natural lenses during a cataract operation, obtain a more efficient and sensitive accommodation with a quick and sufficient pull back power, if the centralizing spring haptics show a z-similar shape with a large square stone bridge.

5 Claims, 4 Drawing Sheets

ACCOMMODATING IO-LENS EYES

CROSS-REFERENCE TO RELATED APPLICATIONS

Not Applicable

STATEMENT REGARDING FEDERALLY SPONSORED RESEARCH

Not Applicable

BACKGROUND OF THE INVENTION

To remove the gray star (muddy natural eye lenses) one replaces the natural eye lens by an artificial one. Such intraocular lenses show normally the shape of a paragraph sign, where the haptics stand-off s-shaped and centralize the lens within the capsular bag. These artificial lenses are very flexible in their wet stage and are therefore foldable to be better implanted through an advantageous small lateral slit of the eye, but they are not deformable any more to change their focus. Since such artificial lenses show an unchangeable focus, the sharpness of before or behind it lying picture points have therefore to be approximate by adjusting glasses. The resulting blurred sight in between causes a remarkable loss of vision comfort, which should be reduced by an optimally accommodating artificial lens, which offer the chance to renounce of any correcting glasses.

Even without diagnosed muddy natural lenses, such a well accommodating artificial lens is ready to be replaced in healthy eyes in the future, to avoid expensive laser corrections of the cornea in case of great short-sightedness and can prevent long-sightedness in old age.

Instead of changing the convexity of an artificial lens one can accommodate only by changing the lens distance from the retina caused by a contracting ciliary muscle, provided it remained undamaged after the removal of the natural lens and is still active.

Concepts of accommodating artificial IO-lenses are already known from the patent applications: Cumming (WO 99/29266 according to his application PCT US98/26171, A61F 2/16, priority Sep. 12, 1997) and of another application of Dr. Helmut Payer, Plantaweg 12 a, CH-7000 Chur/Schweiz (Datasheet: 4351 980414) and WO 9903427. It has to be doubt, if the claim of linkage arms in this last application of which all the following claims depend on is qualified enough for a patent, because such linkage arms are already known from earlier concepts.

BRIEF SUMMARY OF THE INVENTION

FIG. 1 shows an accommodating IO-lens with one pivot on the bridge of its centralizing spring haptic;

FIG. 2 shows an accommodating IO-lens with z-similar shaped centralizing spring haptics, which shows a dislocation;

FIG. 3 shows a deformation of a z-similar shaped centralizing spring haptic with small or great dislocation depending of the contraction of the ciliary muscle.

FIG. 4 shows an artificial IO-lens produced in its harder stage with extended and stretched centralizing spring haptics.

BRIEF DESCRIPTION OF THE SEVERAL VIEWS OF THE DRAWINGS

A detailed description of the invention is hereafter described with specific reference being made to the drawings in which:

DETAILED DESCRIPTION OF THE INVENTION

The aim of a more effective accommodating IO-lens is reached by z-similar shaped centralizing spring haptics according to claim 1. Additional characteristics are explained by the claims 2–5.

Figure 1:
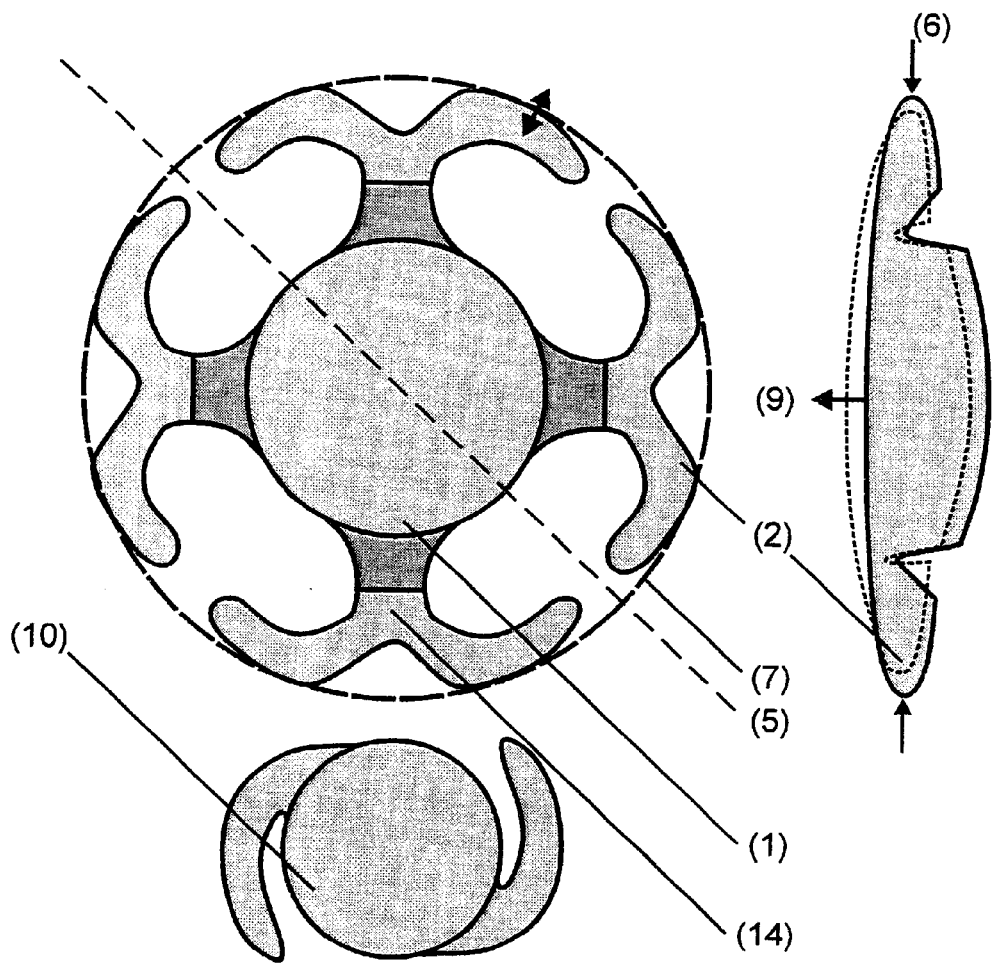

FIG. 1 shows an accommodating intraocular lens 1 with only one pivot on the bridge 14 of each of its four centralizing spring haptics 2 standing off the border of the lens. Through folding line 5 is used for the shutting of the lens before its injection into the capsular bag 7. The capsular bag has a remaining cavity after the removal of the natural lens. The ciliary muscle contracts to a working extent 6 which is a factor in determining the size and direction of the dislocation 9 of the intraocular lens. A common non-accommodating intraocular lens with two s-shaped centralizing spring haptics has the known shape 10.

Figure 2:
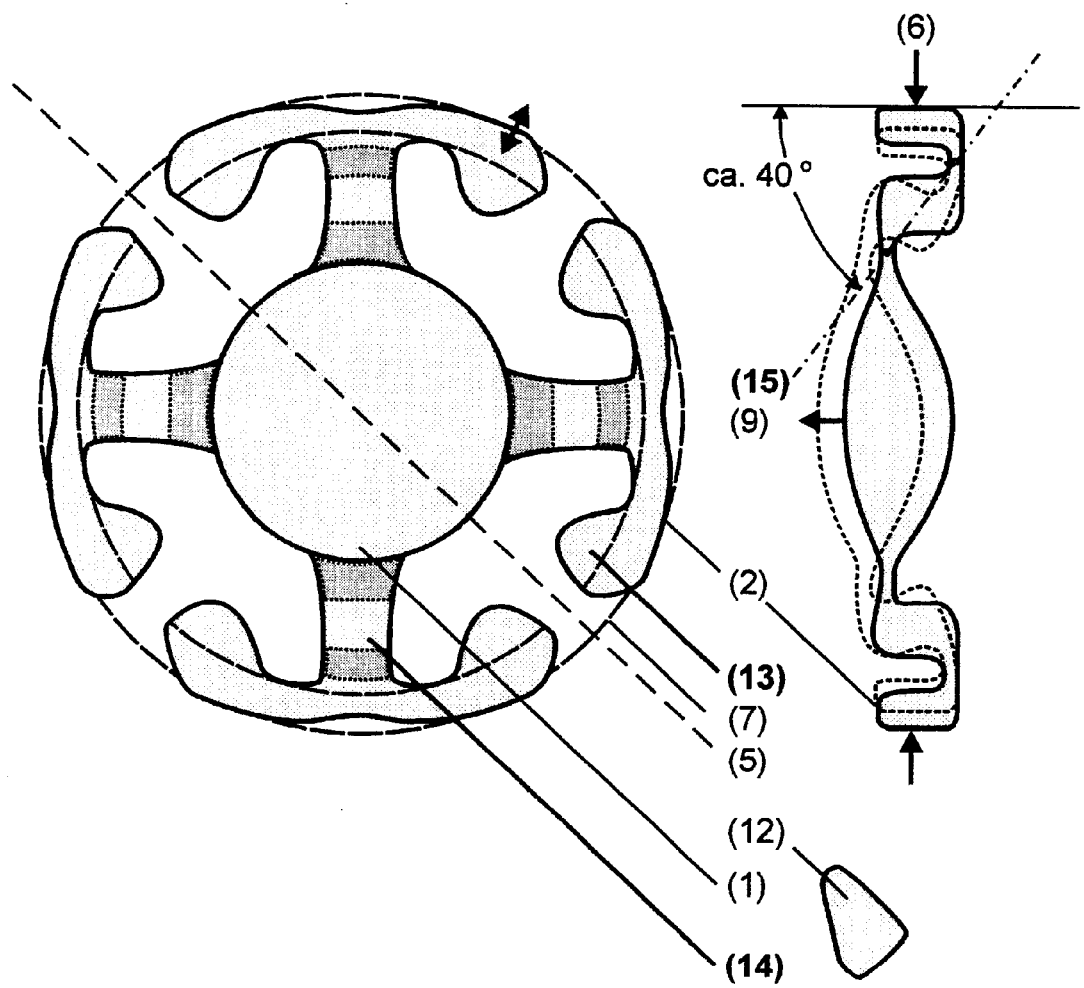

FIG. 2, by z-similar shaped centralizing spring haptics 2, the dislocation 9 is instead impressively enlarged.

The support lobes 13 at the ends of the centralizing spring haptics 2 lean with their back side at the front of the glass body membrane and avoid their inclining.

Figure 3:
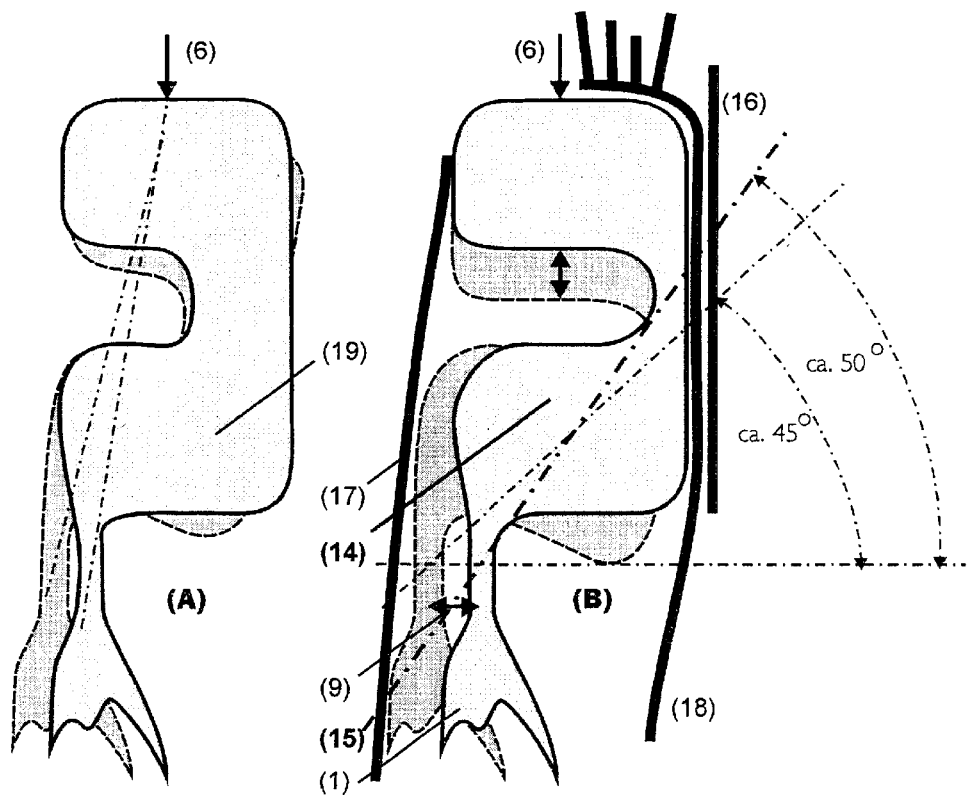

FIG. 3 shows the deformation of z-similar shaped spring haptics by contraction of the ciliary muscle. The angle of the thought connection line 15 between the bridge 14 and the optical axis of the AAIOL consists of ca. 40 to 45 degrees depending of their deformation, therefore the intended maximum and nearly linear sensitivity of this accommodation assembly is reached.

The bridge of the z-similar spring haptics is large square stone shaped, therefore its front side touches the front of the capsular bag 17 and its back side touches the front of the glass body membrane 16. This sustains the relocation of the AAIOL by the back strain of the meridionally enlarged capsular bag caused by its expansion during a willingly induced accommodation to use its back pulling power.

Figure 4:
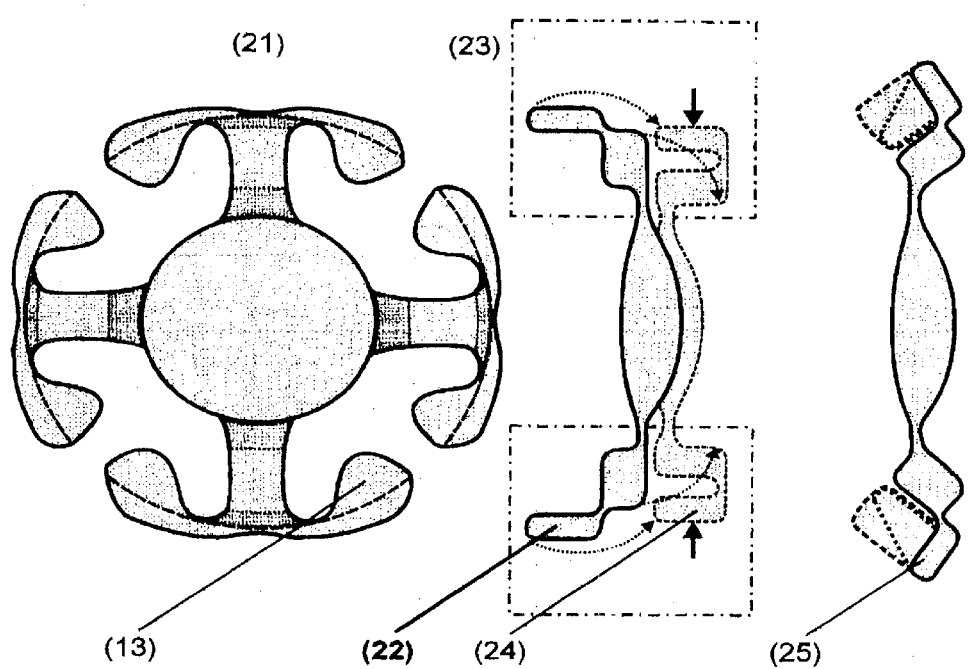

FIG. 4 shows the production form of an AAIOL1 with extended and stretched centralizing spring haptic in its harder stage, that means before its stream treatment to make it soft elastic. Compressed to its z-similar shape after its implantation the AAIOL is pulled back faster from this unnatural struting to its original start shape after a temporary dislocation 22.

If the ciliary muscle is relaxed the compressed elastic centralizing spring haptics pull back themselves into their start position and therefore return the AAIOL in its zero position. To increase the back pulling power of the centralizing spring haptics in spite of their normally used soft elastic lens material after a lens disclosing, they are partially treated by chemical and physical means (by increasing the chemical bonding of the molecules by UV-irradiation or by a partial humidity rejecting a surface coating, which reduces the softening influence of the steam) struting the linkage arms additionally.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. Accommodating IO-lenses for replacement of muddy natural lenses, said natural lenses found inherently in the capsular bag having both inner and outer front and back membranes, said accommodating lenses having an optical axis and a border having centralizing spring haptics standing off therefrom, the centralizing spring haptics characterized by a z-similar cross section.

2. The lenses according to claim 1 wherein the centralizing spring haptics have a large square stone bridge through which a bridge line can be drawn through the center of the square stone bridge and through the center of a part of the haptic which connects the lens to the large square stone bridge, said bridge line forming an angle in the range of approximately 45 degrees in the compressed stage to the optical axis and of approximately 50 degrees in the uncompressed stage to the optical axis.

3. The lenses according to claim 1 characterized by haptics with a bridge with a space filling square stone shape, said bridge has a front side which touches the inner front of the capsular bag and said bridge has a back side which touches the front of the back membrane of the capsular bag, while struting simultaneously the soft lens body to a slightly shorter focus when the centralizing spring haptics are compressed.

4. The lenses according to claim 1 having centralizing spring haptics with free ends and characterized by support lobes on the free ends of the centralizing spring haptics, said free ends are leaned against the back membrane of the capsular bag and are radial with respect to the center of the lens.

5. The lenses according to claim 1 characterized by a harder state after production and before their steam treatment with extended and stretched centralizing spring haptics.

* * * * *